(12) United States Patent
Hall et al.

(10) Patent No.: US 12,285,190 B2
(45) Date of Patent: *Apr. 29, 2025

(54) ASYMMETRIC SHAFT SEAL

(71) Applicant: Cilag GmbH International, Zug (CH)

(72) Inventors: Steven G. Hall, Lebanon, OH (US); Joseph Thomas Mozloom, Jr., Cincinnati, OH (US); Christopher W. Birri, West Chester, OH (US); Daniel J. Prenger, Loveland, OH (US); Ryan Alan Klenke, St. Henry, OH (US)

(73) Assignee: Cilag GmbH International, Zug (CH)

( * ) Notice: Subject to any disclaimer, the term of this patent is extended or adjusted under 35 U.S.C. 154(b) by 544 days.

This patent is subject to a terminal disclaimer.

(21) Appl. No.: 17/079,637

(22) Filed: Oct. 26, 2020

(65) Prior Publication Data

US 2021/0038258 A1 Feb. 11, 2021

Related U.S. Application Data

(62) Division of application No. 16/009,591, filed on Jun. 15, 2018, now Pat. No. 10,820,924.

(51) Int. Cl.
*A61B 17/34* (2006.01)
*A61B 17/02* (2006.01)
*A61M 39/06* (2006.01)

(52) U.S. Cl.
CPC ...... *A61B 17/3462* (2013.01); *A61B 17/0218* (2013.01); *A61B 17/3423* (2013.01);
(Continued)

(58) Field of Classification Search
CPC . A61B 17/34; A61B 17/3462; A61B 17/0218; A61B 17/3423; A61M 39/0693
See application file for complete search history.

(56) References Cited

U.S. PATENT DOCUMENTS 5,242,412 A * 9/1993 Blake, III ............. A61M 39/06
604/167.01
5,380,288 A 1/1995 Hart et al.
(Continued)

FOREIGN PATENT DOCUMENTS

CN 106255469 A 12/2016
EP 2814559 12/2014
(Continued)

OTHER PUBLICATIONS

Chinese Office Action from corresponding CN Application No. 2019800396828 mailed May 23, 2019.

*Primary Examiner* — Ellen C Hammond
(74) *Attorney, Agent, or Firm* — Vorys, Sater, Seymour and Pease LLP (57) ABSTRACT

An integral seal system includes a body that defines a central opening, and an asymmetric seal extending into the central opening and including a diaphragm and an annular flange that extends between the body and the diaphragm, wherein the diaphragm has a cross-sectional thickness larger than a cross-sectional thickness of the annular flange. A duckbill seal extends distally from a bottom of the body and defines one or more parting lines that separate opposing seal flaps. The diaphragm complements insertion and extraction drag forces generated by the duckbill seal against a surgical tool shaft extended therethrough such that total insertion and extraction drag forces generated by the integral seal system are equalized.

19 Claims, 9 Drawing Sheets

(52) U.S. Cl.
CPC . *A61M 39/0693* (2013.01); *A61M 2039/0626* (2013.01); *A61M 2039/0646* (2013.01); *A61M 2039/0673* (2013.01); *A61M 2039/0686* (2013.01)

(56) References Cited

U.S. PATENT DOCUMENTS

| | | | |
|---|---|---|---|
| 5,496,280 A * | 3/1996 | Vandenbroek | A61M 39/06 604/167.03 |
| 5,584,850 A | 12/1996 | Hart | |
| 5,906,595 A | 5/1999 | Powell | |
| 9,295,523 B2 | 3/2016 | Blumenkranz et al. | |
| 2005/0209607 A1 | 9/2005 | Lipchitz et al. | |
| 2006/0224164 A1* | 10/2006 | Hart | A61B 17/3498 606/108 |
| 2008/0065111 A1 | 3/2008 | Blumenkrantz | |
| 2013/0211423 A1 | 8/2013 | Blumenkrantz | |
| 2018/0008313 A1 | 1/2018 | Augelli et al. | |

FOREIGN PATENT DOCUMENTS

| | | |
|---|---|---|
| JP | H1170116 A | 3/1999 |
| WO | 2011044127 A1 | 4/2011 |
| WO | 2015142794 A1 | 9/2015 |

* cited by examiner

ASYMMETRIC SHAFT SEAL

BACKGROUND

During laparoscopic surgery, one or more small incisions are formed in a patient's skin and a trocar assembly is inserted through the incision to provide access to an internal body cavity, such as the patient's abdomen. The trocar assembly operates as a pathway that can be used to introduce various surgical instruments and tools into the abdomen.

A trocar assembly generally includes a trocar and a seal assembly operatively coupled to or forming part of the trocar. The trocar includes a trocar housing and a cannula that extends distally from the trocar housing and provides the pathway into the patient's abdomen. The seal assembly includes one or more seals that help maintain insufflation of the penetrated body cavity and also seal about surgical tools extended through the trocar and into the patient's abdomen. In some applications, the seal assembly may comprise a seal cartridge at least partially received within the trocar housing.

Trocar seal assemblies commonly include a "duckbill" seal, which is normally closed until penetrated by the shaft of a surgical tool, at which point the duckbill seal receives and engages the outer circumference of the tool shaft as the surgical tool is introduced into the patient's abdomen. Because of its distally-protruding design, the duckbill seal typically generates smaller drag forces against the tool shaft while inserting the surgical tool as compared to the drag forces generated while extracting the surgical tool.

The variance between insertion and extraction drag forces can cause hysteresis, as a user (e.g., a surgeon) does not typically or consciously anticipate the added amount of force required to extract the surgical tool as compared to the force required to insert the surgical tool. In severe cases, this can cause inadvertent damage or injury to patient tissue. For robotic surgical applications, dissimilar insertion and extraction drag forces requires the robot to be programmed and calibrated separately for insertion and extraction movements to compensate for the different drag forces in each direction, thus further complicating the system.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to trocar assemblies and, more particularly, to an integral seal system designed to equalize insertion and extraction drag forces generated against a surgical tool shaft.

The embodiments presented herein described an integral seal system that is designed to equalize surgical tool insertion and extraction forces. More specifically, the integral seal system may be included in a trocar assembly that includes a trocar having a trocar housing and a cannula that extends distally from the trocar housing. The integral seal system may be positioned within a central passageway extending axially through the trocar and may be engageable against a surgical tool shaft extended therethrough. The integral seal system may include an asymmetric seal and a duckbill seal arranged distal to the asymmetric seal, and the asymmetric seal defines a diaphragm that protrudes proximally and operates to complement insertion and extraction drag forces generated by the duckbill seal against the surgical tool shaft such that total insertion and extraction drag forces generated by the integral seal system are equalized.

Figure 1:
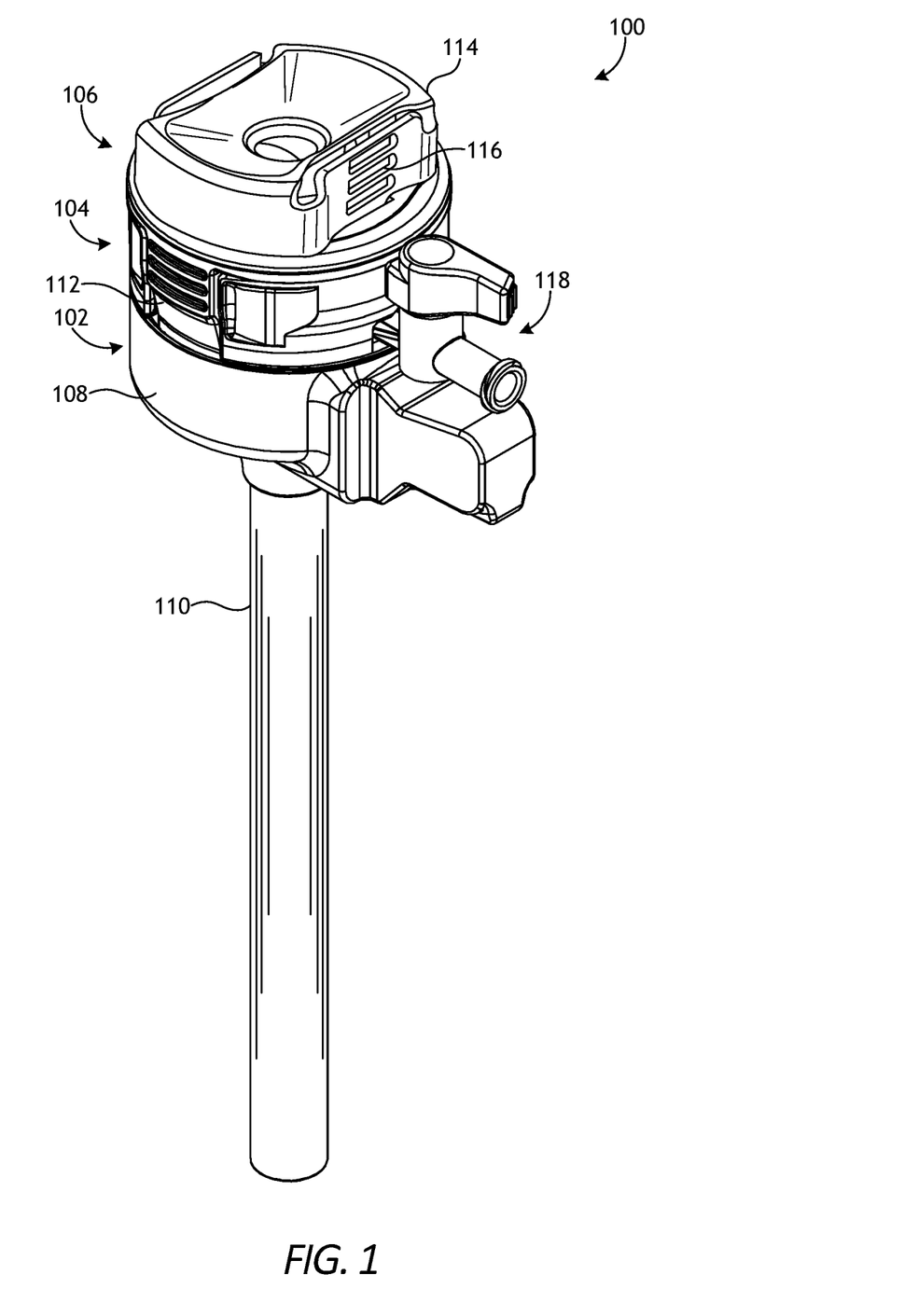
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example of a trocar assembly that can suitably incorporate the principles of the present disclosure. Those skilled in the art will readily appreciate that many alternative designs and configurations of the trocar assembly 100 may be employed or incorporated, without departing from the scope of this disclosure.

As illustrated, the trocar assembly 100 may include a trocar 102, a seal cartridge 104 releasably coupled to the trocar 102, and a trocar bushing 106 that may be releasably coupled to a proximal end of the seal cartridge 104. The trocar 102 includes a trocar housing 108 and a cannula 110 that extends distally from the trocar housing 108. In some embodiments, the cannula 110 may comprise an integral extension of the trocar housing 108. In other embodiments, the trocar housing 108 and the cannula 110 may comprise two separate components that are mated to one another. The trocar 102 may be made of any rigid or semi-rigid material, such as a metal or a plastic.

The seal cartridge 104 may be at least partially received within the trocar housing 108 and include one or more actuatable latches 112 (one shown and one hidden) that releasably couple the seal cartridge 104 to the trocar housing 108. The trocar bushing 106 may include a bushing housing 114 that provides one or more actuatable latches 116 (one shown and one hidden) that releasably couple the trocar bushing 106 to the seal cartridge 104. In some embodiments, however, the trocar bushing 106 may be omitted from the trocar assembly 100, without departing from the scope of the disclosure.

The trocar assembly 100 may also include an insufflation valve 118 (e.g., a stopcock valve) operable to regulate the influx of an insufflation fluid (e.g. carbon dioxide) used to elevate the interior walls of an inner body cavity (e.g., the abdomen) of a patient. In the illustrated embodiment, the insufflation valve 118 is coupled to the seal cartridge 104 or otherwise forms an integral part thereof. In other embodiments, however, the insufflation valve 118 may alternatively be coupled to the trocar housing 108 or may form an integral part thereof.

Figure 2:
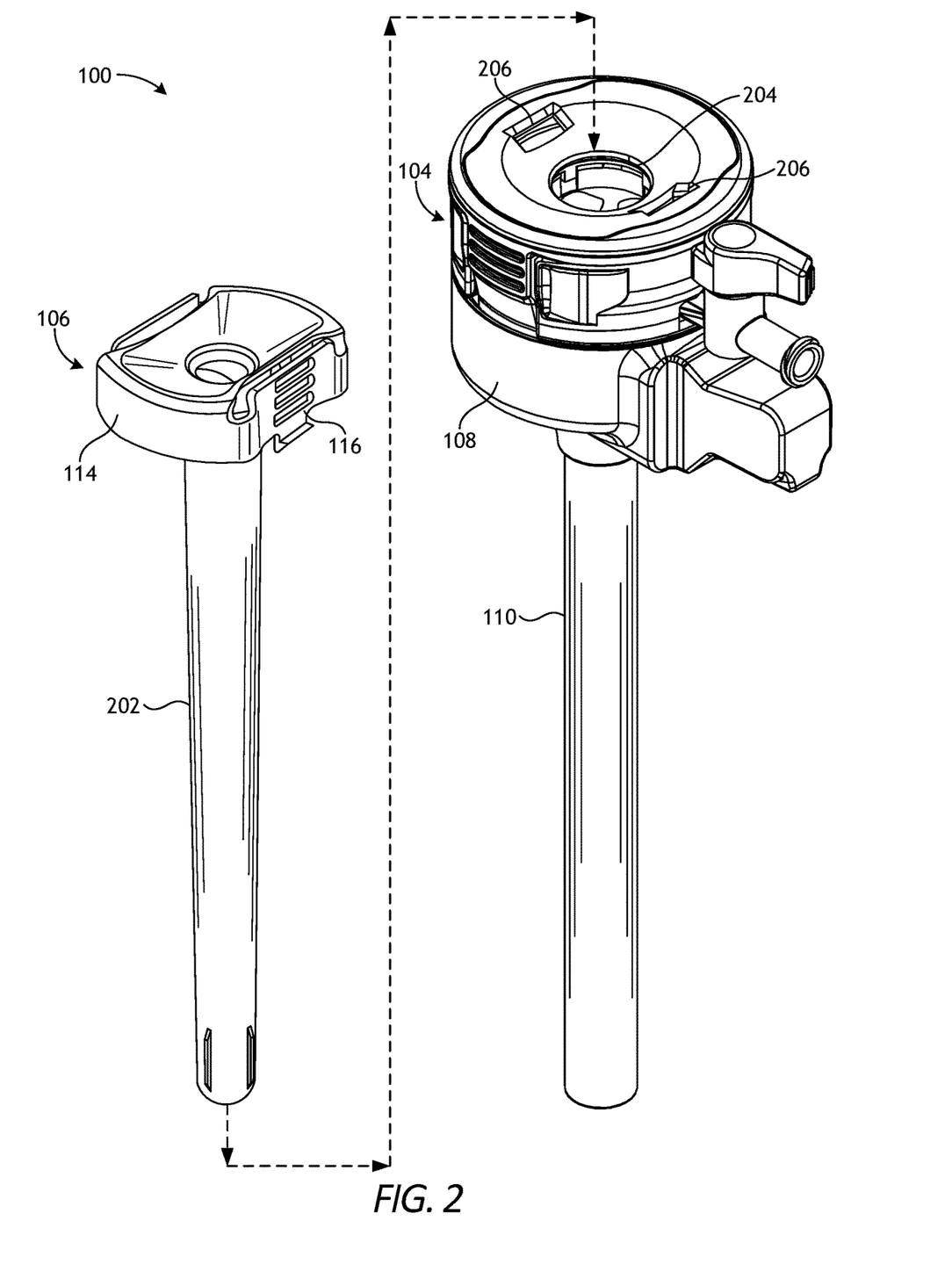
FIG. 2 is a partial exploded view of the trocar assembly of FIG. 1.

FIG. 2 is a partial exploded view of the trocar assembly 100 of FIG. 1. More particularly, the trocar bushing 106 is shown separated from the seal cartridge 104. As illustrated, the trocar bushing 106 includes a reducer shaft 202 that extends distally from the bushing housing 114. To couple the trocar bushing 106 to the seal cartridge 104, the reducer shaft 202 may be extended into a central orifice 204 defined in the proximal end of the seal cartridge 104. The trocar bushing 106 may then be advanced distally to extend the reducer shaft 202 through the seal cartridge 104 and the trocar housing 108, and ultimately into the interior of the trocar cannula 110. The trocar bushing 106 may be releasably coupled to the seal cartridge 104 by receiving the actuatable latches 116 of the bushing housing 114 into corresponding latch apertures 206 defined on the proximal end of the seal cartridge 104.

The trocar bushing 106 and the corresponding reducer shaft 202 may operate to reduce the effective inner diameter of the trocar assembly 100, which enables the trocar assembly 100 to accommodate and center reduced-diameter surgical tools. For example, the trocar bushing 106 may be sized to accommodate surgical tools that have an outer diameter of 5 mm. When larger-diameter surgical tools are used, such as surgical tools that have an outer diameter of 8 mm or 12 mm, the trocar bushing 106 may be omitted and such larger-diameter surgical tools may be introduced into the trocar assembly 100 via the central orifice 204.

Figure 3:
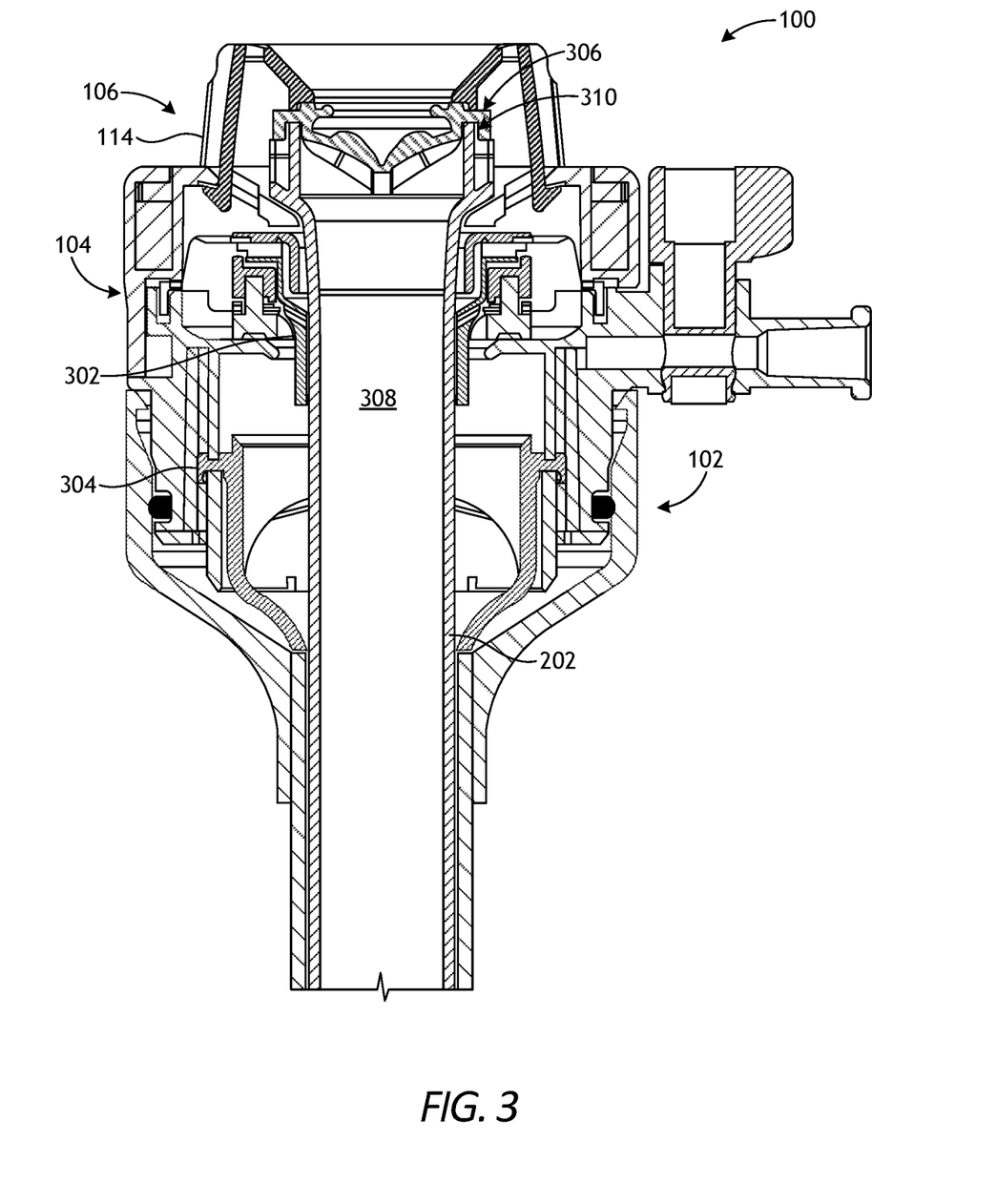
FIG. 3 is an enlarged cross-sectional side view of a portion of the trocar assembly of FIGS. 1 and 2.

FIG. 3 is an enlarged cross-sectional side view of a portion of the assembled trocar assembly 100. As illustrated, the seal cartridge 104 may include one or more seals, namely, a first or "proximal" seal 302 and a second or "distal" seal 304. The first and second seals 302, 304 facilitate selective sealing of the trocar assembly 100 during operation. In the illustrated embodiment, the first and second seals 302, 304 receive and engage the outer surface of the reducer shaft 202 as extended through the seal cartridge 104. In operation, the first seal 302 may be configured to sealingly engage the outer surface of the reducer shaft 202. While two seals 302, 304 are depicted in FIG. 3, the seal cartridge 104 may alternatively include more or less than two seals, without departing from the scope of the disclosure.

In some embodiments, the first seal 302 may comprise an expandable iris seal configured to receive and expand radially to seal against the reducer shaft 202 extended through the seal cartridge 104. Alternatively, in embodiments that omit the trocar bushing 106, the first seal 302 may seal about the outer surface of a surgical tool shaft (not shown). The second seal 304 may be configured to help maintain insufflation when not penetrated, but may also seal against the outer circumference of the reducer shaft 202 when the trocar bushing 106 is used. In some embodiments, as illustrated, the second seal 304 may comprise a duckbill seal, as generally known to those skilled in the art.

The seals 302, 304 may be made of an elastic or pliable material. Suitable elastic or pliable materials include, but are not limited to, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, ethylene vinyl acetate, nylon, vinyl, spandex, polyurethane, polyethylene, polypropylene, polyisoprene, or any combination thereof.

According to embodiments of the present disclosure, the trocar assembly 100 may further include a shaft seal referred to herein as an integral seal system 306 positioned within a central passageway 308 extending axially through the trocar assembly 100. The central passageway 308 may comprise any elongate pathway that extends axially through the trocar assembly 100 to receive and guide the surgical tool shaft as it is inserted and extracted. In the illustrated embodiment, for example, the central passageway 308 is defined by the trocar bushing 106 as extended through the seal cartridge 104 and the trocar 102. More particularly, the central passageway 308 is at least partially defined by the bushing housing 114 and the interior of the reducer shaft 202.

The integral seal system 306 may be positioned within the central passageway 308 and otherwise arranged to sealingly engage the outer surface of a surgical tool shaft extended through the central passageway 308. More specifically, as a surgical tool shaft (not shown) is introduced into the central passageway 308, the integral seal system 306 operates to seal about the outer circumferential surface thereof. The integral seal system 306 may be made of any of the elastic or pliable materials mentioned herein for the seals 302, 304. In the illustrated embodiment, the integral seal system 306 is arranged at a proximal end 310 of the reducer shaft 202 and, in some embodiments, may be retained between and otherwise interpose the proximal end 310 of the reducer shaft 202 and a portion of the bushing housing 114. In other embodiments, however, the integral seal system 306 may be arranged at any location along the central passageway 308, without departing from the scope of the disclosure.

Those skilled in the art will readily appreciate that the central passageway 308 may be defined by other component parts of the trocar assembly 100, without departing from the scope of the disclosure. As described below, for example, embodiments are contemplated herein where the trocar bushing 106 is omitted and the central passageway 308 is alternatively defined contiguously through the seal cartridge 104 and the trocar 102. In such embodiments, the integral seal system 306 may be arranged within the seal cartridge 104, for example, or another location within the central passageway 308. In yet other embodiments described herein, it is contemplated that the seal cartridge 104 and the trocar bushing 106 may both be omitted from the trocar assembly 100, and the central passageway 308 may alternatively be defined through the trocar housing 108 and the cannula 110. In such embodiments, the integral seal system 306 may be arranged coupled to the trocar housing 108 or another location along the central passageway 308.

Figure 4A:
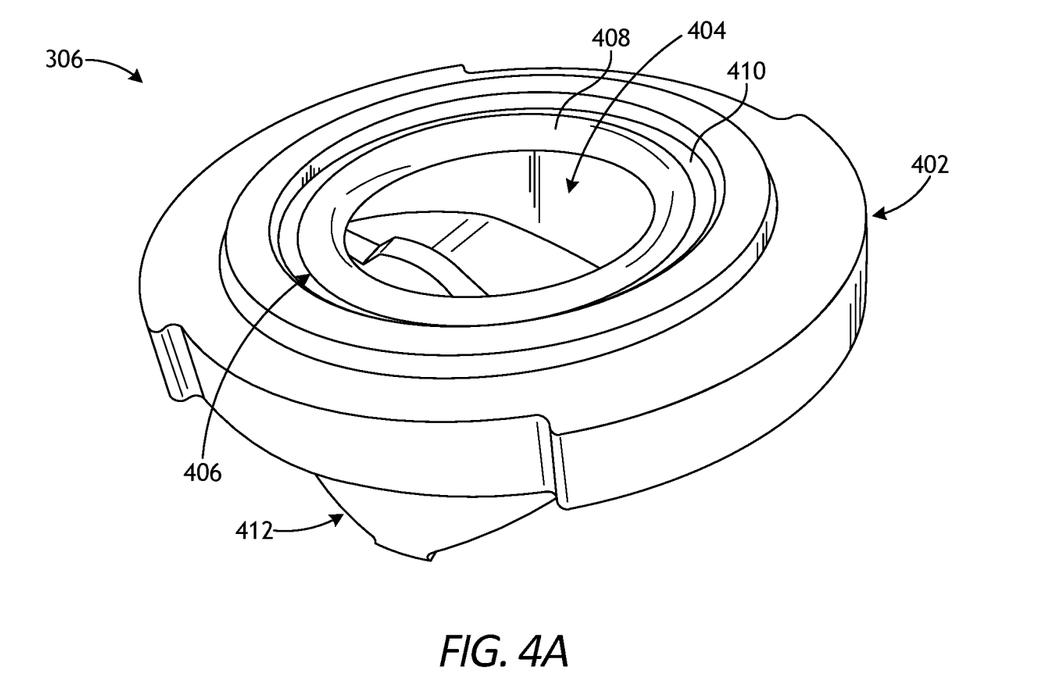
FIGS. 4A and 4B are isometric top and bottom views, respectively, of the integral seal system of FIG. 3.
Figure 4B:
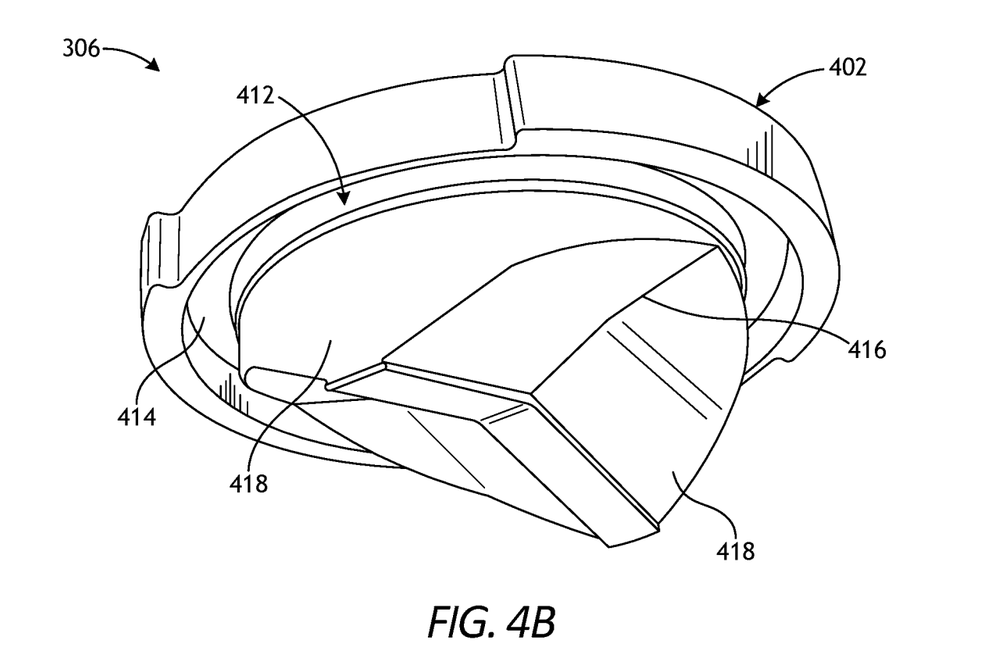

FIGS. 4A and 4B are isometric top and bottom views, respectively, of one example of the integral seal system 306, according to one or more embodiments. Referring first to FIG. 4A, the integral seal system 306 may provide a generally circular body 402 that defines a central opening 404. In other embodiments, the body 402 may exhibit other cross-sectional shapes, such as polygonal or oval, without departing from the scope of the disclosure. An asymmetric seal 406 may be defined by the body 402 and extend radially into the central opening 404. As illustrated, the asymmetric seal 406 may comprise a diaphragm 408 and an annular flange 410 that extends between the body 402 and the diaphragm 408. As discussed below, the diaphragm 408 may be configured to engage and seal against the outer circumference of an object (e.g., a surgical tool shaft) extended through the center opening 404 and otherwise penetrating the integral seal system 306.

In FIG. 4B, a duckbill seal 412 (alternately referred to as a "check valve") may be provided on a bottom 414 of the body 402 and otherwise extend distally from the bottom 414. The duckbill seal 412 may define one or more parting lines 416 (one shown) that separate opposing seal flaps 418. In its relaxed, unpenetrated state, the seal flaps 418 remain closed (sealed) along the parting line(s) 416 and the duckbill seal 412 thereby helps to maintain insufflation. As an object (e.g., a surgical tool shaft) is extended through the center opening 404, the duckbill seal 412 may open along the parting line(s) 416 as the seal flaps 418 separate to engage and seal against the outer circumference of the object.

While the duckbill seal 412 is depicted with a particular configuration and design, those skilled in the art will readily recognize that other configurations and designs may alternatively be employed, without departing from the scope of the disclosure. For example, in some embodiments, the duckbill seal 412 may include two bisecting parting lines (e.g., "double slit") that define four or more seal flaps.

Figure 5:
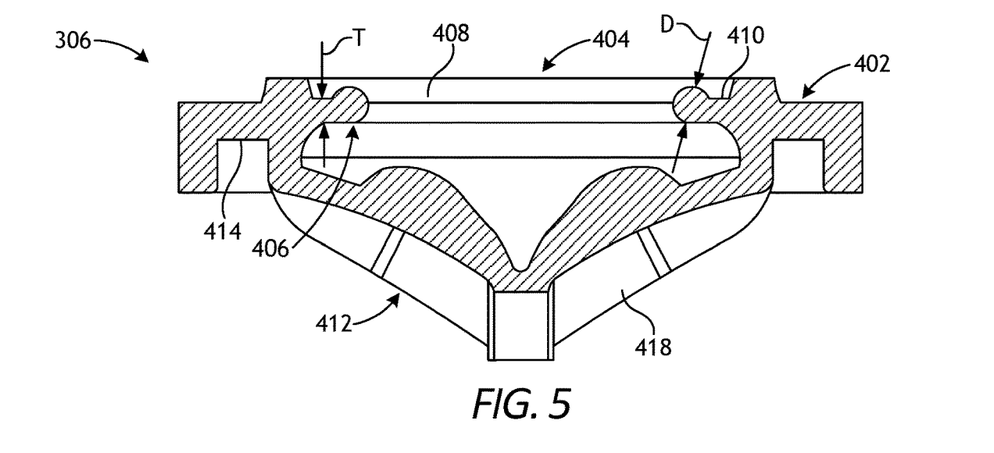
FIG. 5 is a cross-sectional view of the integral seal system perpendicular to a parting line of the integral seal system.

FIG. 5 is a cross-sectional view of the integral seal system 306 perpendicular to the parting line 416 of FIG. 4B, according to one or more embodiments. As illustrated, the asymmetric seal 406 extends radially into the central opening 404 and terminates with the diaphragm 408, and the duckbill seal 412 extends distally from the bottom 414 of the body 402. In some embodiments, the integral seal system 306 may be molded as single structure that includes both the asymmetric and duckbill seals 406, 412. In other embodiments, however, the integral seal system 306 may comprise a multi-component structure. In such embodiments, the duckbill seal 306, for example, may be overmolded onto the body 402. Alternatively, the duckbill seal 306 may be attached to the body 402 using for example, an adhesive, ultrasonic welding, one or more mechanical fasteners, an interference fit, a snap fit, or any combination thereof.

As an object, such as a surgical tool shaft, is extended through the center opening 404, drag forces will be generated as the asymmetric and duckbill seals 406, 412 independently engage the outer circumference of the tool shaft. Due to the distally-extending construction and design of the duckbill seal 412, insertion and extraction drag forces generated by the duckbill seal 412 against the tool shaft will be dissimilar. More specifically, drag forces generated by the seal flaps 418 engaging the outer circumference of the tool shaft may be smaller (lower) as the tool shaft is inserted (i.e., advanced distally) as compared to drag forces generated as the tool shaft is extracted (i.e., retracted proximally).

Dissimilar insertion and extraction drag forces can result in hysteresis since a user (e.g., a surgeon) must actively adjust the insertion and extraction forces applied to the surgical tool during use. Consequently, the user has to mentally gauge the amount of force required to insert or extract a surgical tool, which can adversely affect controllability and potentially cause damage or injury to the patient. For robotic surgical applications, the robot is powered by one or more motors operable to push and pull on the surgical tool. Dissimilar insertion and extraction drag forces require the robot to be programmed and calibrated differently for the opposing movements such that an equal but opposite command input velocity for tool insertion and extraction results in equal and opposite physical performance of the tool.

The asymmetric seal 406 may be configured to compensate for the dissimilar insertion and extraction drag forces generated by the duckbill seal 412 and thereby provide the integral seal system 306 with a "total" drag force that is consistent (uniform) during tool insertion and extraction. To accomplish this, the asymmetric seal 406 may be tuned and otherwise optimized to generate larger drag forces during tool insertion, and smaller drag forces during tool extraction. When the drag forces generated by the asymmetric seal 406 are combined with the drag forces generated by the duckbill seal 412, the net drag forces generated by the integral seal system 306 as a whole may be equal (or close to equal) in both directions for tool insertion and extraction. As a result, operation of the surgical tool by a user (e.g., a surgeon) may be more consistent and reliable, and for robotic surgical applications there may be no need to calibrate or program different speeds for tool insertion and extraction movement.

To enable the asymmetric seal 406 to generate larger tool insertion drag forces and smaller tool extraction drag forces, the diaphragm 408 may extend (protrude or project) proximally and otherwise away from the duckbill seal 412. Said differently, in its relaxed state, the diaphragm 408 may be configured to project from the flange 410 proximally or in the proximal direction. In some embodiments, as illustrated, the diaphragm 408 may exhibit a bulbous or spherical cross-section. In other embodiments, however, the diaphragm 408 may exhibit other cross-sectional shapes such as, but not limited to, polygonal, pyramidal, conical, frustoconical, ovoid, or any combination thereof.

In the illustrated embodiment, the diaphragm 408 has a spherical or circular cross-section and exhibits a diameter D. The magnitude of the diameter D and the cross-sectional circumferential connection location to the annular flange 310, as well as the size and extent of the annular flange 310 (e.g., a thickness T) may be varied to tune the asymmetric seal 406 to generate insertion and extraction drag forces that when superimposed with the corresponding insertion and extraction drag forces of the duckbill seal 412, the net total insertion and extraction drag for of the integral seal system 306 may be equal.

As used herein, the terms "equal" or "equalize" do not necessarily mean exactly equal or exactly equalized. As described herein, for instance, the asymmetric seal 406 may operate to offset or complement the drag forces generated by the duckbill seal 412, such that the net drag forces generated by the integral seal system 306 as a whole may be "equal" or "equalized." This does not mean that the net insertion and extraction drag forces are exactly equal or exactly equalized, although that certainly may be the case. Rather, equalizing the net insertion and extraction drag forces refers to bringing the total insertion drag force closer in magnitude to the total extraction drag force, or vice versa, through operation of the asymmetric seal 406.

Figure 6A:
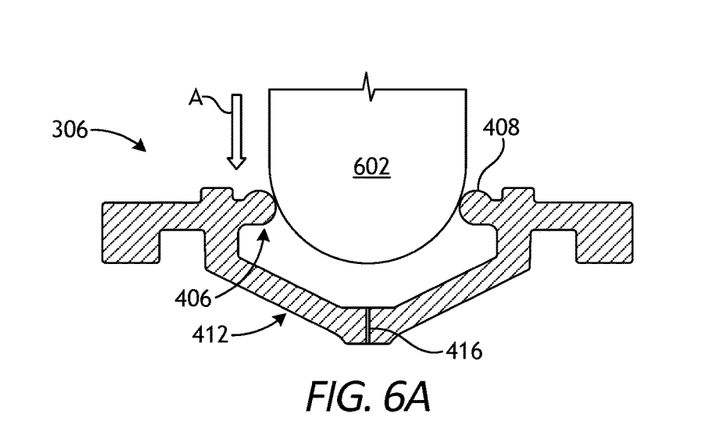
FIGS. 6A-6E are progressive cross-sectional side views of the integral seal system during example operation.
Figure 6B:
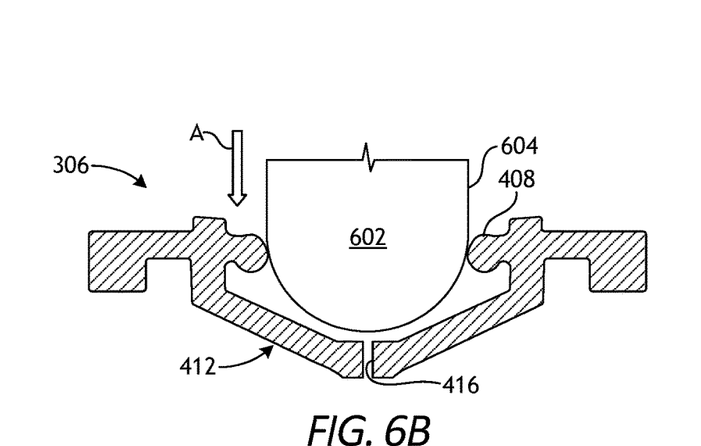
Figure 6C:
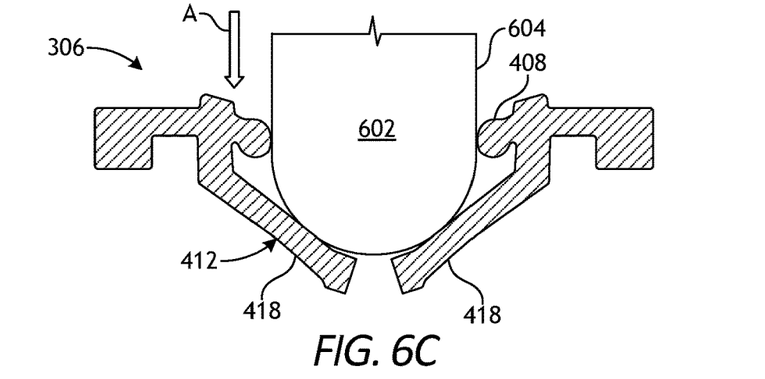
Figure 6D:
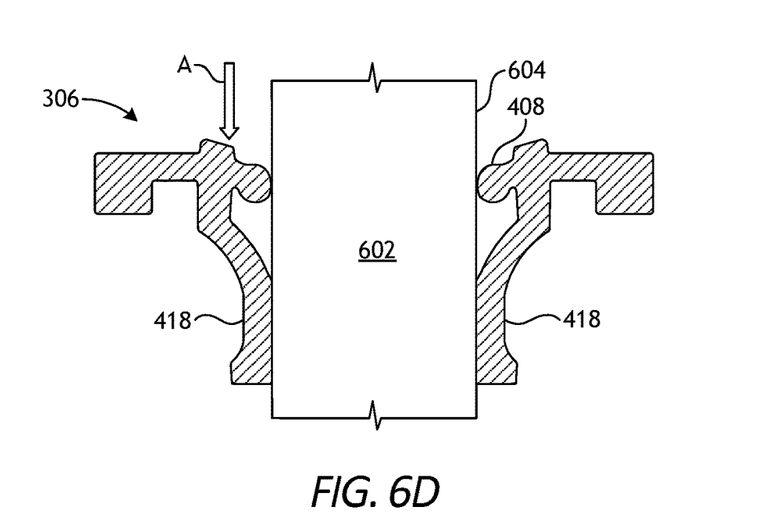
Figure 6E:
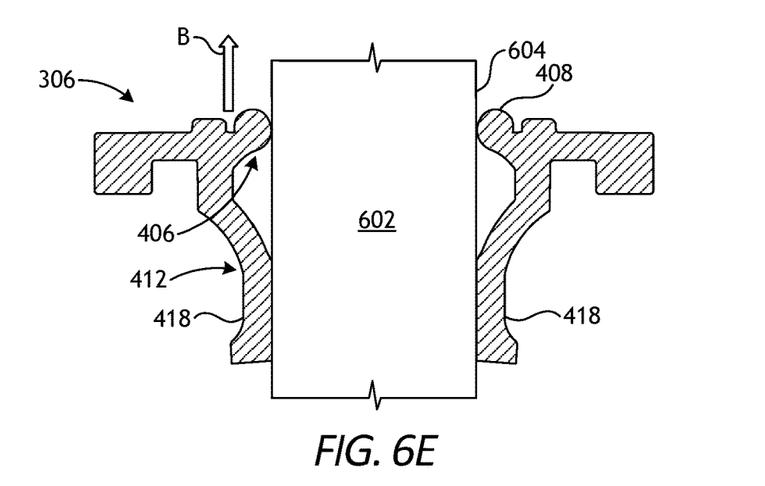

FIGS. 6A-6E are progressive cross-sectional side views of the integral seal system 306 during example operation, according to one or more embodiments. More specifically, FIGS. 6A-6D depict an example surgical tool shaft 602 in the process of being inserted (i.e., distally advanced) into the integral seal system 306, and FIG. 6E depicts the shaft 602 being extracted (i.e., proximally retracted) from the integral seal system 306. In FIG. 6A, the shaft 602 is advanced distally toward the integral seal system 306, as indicated by the arrow A. Before the shaft 602 penetrates the integral seal system 306, the diaphragm 408 projects proximally in its relaxed state. As mentioned above, this enables the asymmetric seal 406 to have larger tool insertion drag forces as compared to drag forces generated during tool extraction. Moreover, before the shaft 602 penetrates the integral seal system 306, the duckbill seal 412 remains closed at the parting line(s) 416 and helps maintain insufflation.

In FIG. 6B, the shaft 602 has advanced distally A into the integral seal system 306 a short distance and the diaphragm 408 has engaged an outer surface 604 of the shaft 602. The engagement between the diaphragm 408 and the outer surface 604 provides a fluid seal that prevents fluids (i.e., gases and liquids) from migrating past that location in either direction. Moreover, the friction generated by the diaphragm 408 against the shaft 602 causes the diaphragm 408 to flex distally, which generates an insertion drag force against the outer surface 604. At this point, the duckbill seal 412 may also start to open at the parting line 416 as a result of a radial load assumed by the diaphragm 408, which is partially transferred to the duckbill seal 412.

In FIG. 6C, the shaft 602 has advanced distally A even further into the integral seal system 306 and now engages the inner walls of the duckbill seal 412 and, more particularly, the inner walls of the seal flaps 418. The insertion drag force generated by the diaphragm 408 against the outer surface 604 of the shaft 602 may be constant as the shaft 602 continues its distal movement. Additional insertion drag forces are incurred as the shaft 602 advances through the duckbill seal 412 and the seal flaps 418 engage the outer surface 604 of the shaft 602. However, since the seal flaps 418 are designed to protrude (extend) distally, the insertion drag forces generated by the duckbill seal 412 are smaller as compared to the extraction drag forces when extracting the shaft 602 proximally.

In FIG. 6D, the shaft 602 has advanced distally A to fully penetrate the integral seal system 306 and fully engage the inner walls of the seal flaps 418. The insertion drag forces generated by the diaphragm 408 and the seal flaps 418 now combine to provide a total insertion drag force generated by the integral seal system 306 against the shaft 602. The insertion drag forces generated by the diaphragm 408 and the seal flaps 418 against the outer surface 604 of the shaft 602 may be constant as the shaft 602 continues distal movement.

In FIG. 6E, the shaft 602 is depicted in the process of being extracted from the integral seal system 306 in the proximal direction, as indicated by the arrow B. As the shaft 602 reverses direction, the friction generated by the diaphragm 408 against the shaft 602 causes the diaphragm 408 to flex proximally, which generates an extraction drag force against the outer surface 604. Since the diaphragm 408 naturally protrudes in the proximal direction B, the extraction drag forces generated by the asymmetric seal 406 may be smaller than its insertion drag forces. Additional extraction drag forces are generated by the duckbill seal 412 as the seal flaps 418 continue to engage the outer surface 604 of the shaft 602. Since the seal flaps 418 naturally extend distally, the extraction drag forces generated by the duckbill seal 412 may be larger than its insertion drag forces.

The extraction drag forces generated by the diaphragm 408 and the seal flaps 418 combine to provide a total extraction drag force generated by the integral seal system 306 against the shaft 602. Since the asymmetric seal 406 is designed to complement (offset) the insertion and drag forces of the duckbill seal 412, the total insertion and extraction drag forces of the integral seal system 306 may be equalized and otherwise equal in both directions. Consequently, a user (e.g., a surgeon) or a robot may apply the same or equal amount of force on the shaft 602 to insert or extract the surgical tool through the integral seal system 306.

Figure 7:
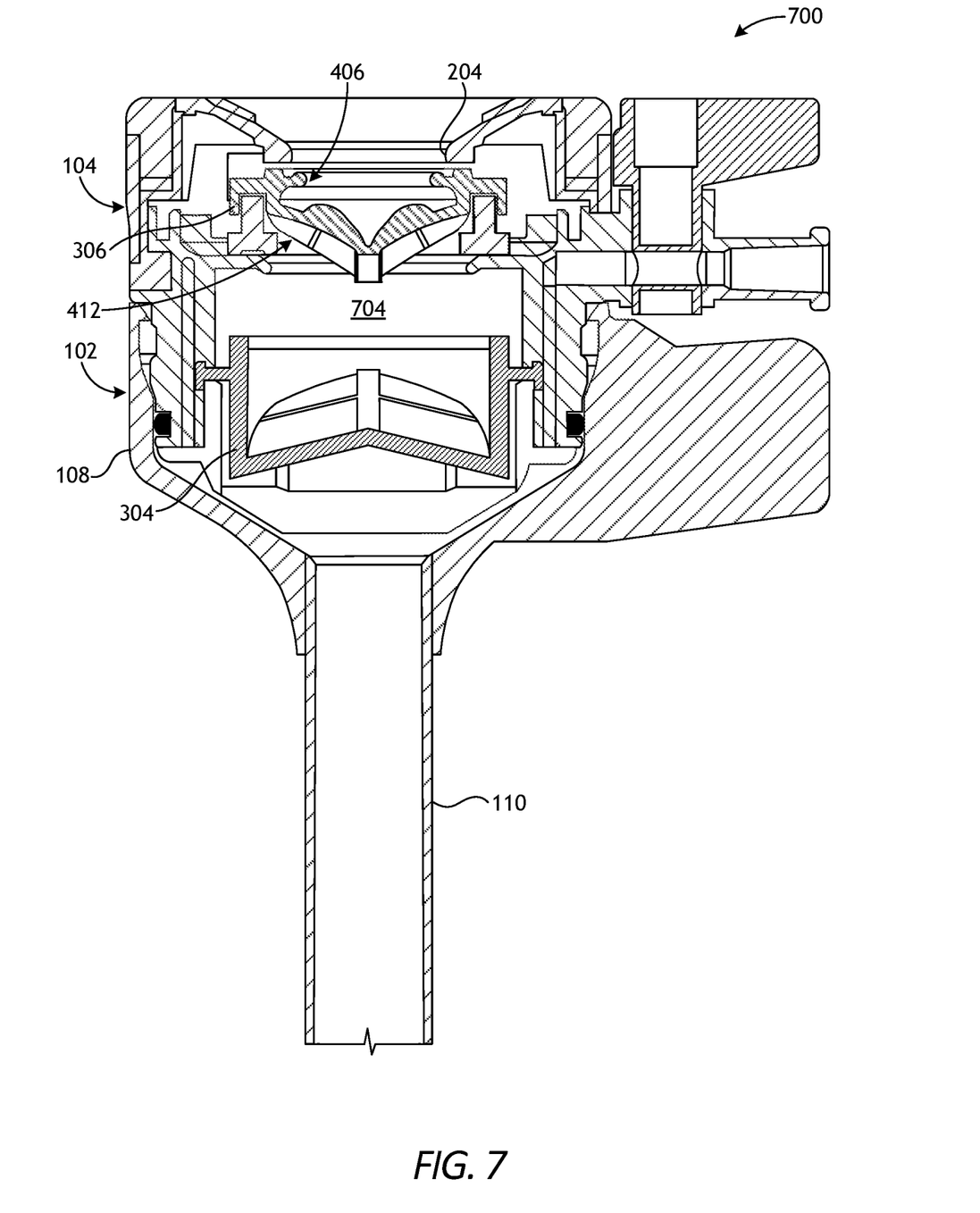
FIG. 7 is an enlarged cross-sectional side view of another example, trocar assembly that may incorporate the principles of the present disclosure.

FIG. 7 is an enlarged cross-sectional side view of another trocar assembly 700 that may incorporate the principles of the present disclosure, according to one or more embodiments. The trocar assembly 700 may be similar in some respects to the trocar assembly 100 of FIGS. 1-3 and therefore may be best understood with reference thereto, where like numerals will represent like components not described again in detail. Similar to the trocar assembly 100 of FIGS. 1-3, the trocar assembly 700 may include the trocar 102 and the seal cartridge 104 at least partially received within the trocar housing 108. Unlike the trocar assembly 100 of FIGS. 1-3, however, the trocar bushing 106 (FIGS. 1-3) is omitted from the trocar assembly 700, and the first seal 302 (FIG. 3) of the seal cartridge 104 in FIG. 3 has been replaced with the integral seal system 306, as generally described above.

The integral seal system 306 is positioned within a central passageway 704 extending axially through the trocar assembly 700. Similar to the central passageway 308 of FIG. 3, the central passageway 704 comprises an elongate pathway that extends axially through the trocar assembly 700 and provides a conduit to guide and introduce surgical tools into an internal body cavity of a patient. In the illustrated embodiment, the central passageway 704 is contiguously defined by the seal cartridge 104 and the trocar 102. Surgical tools may be introduced into the trocar 102 and extended into the cannula 110 by extending through the central orifice 204 and successively penetrating the integral seal system 306 and the second seal 304. In such embodiments, the asymmetric seal 406 may be designed and optimized to complement (offset) the insertion and extraction drag forces generated by both the duckbill seal 412 and the second seal 304. Consequently, the asymmetric seal 406 may be configured to equalize the net drag forces against the surgical tool shaft during insertion and extraction.

Figure 8:
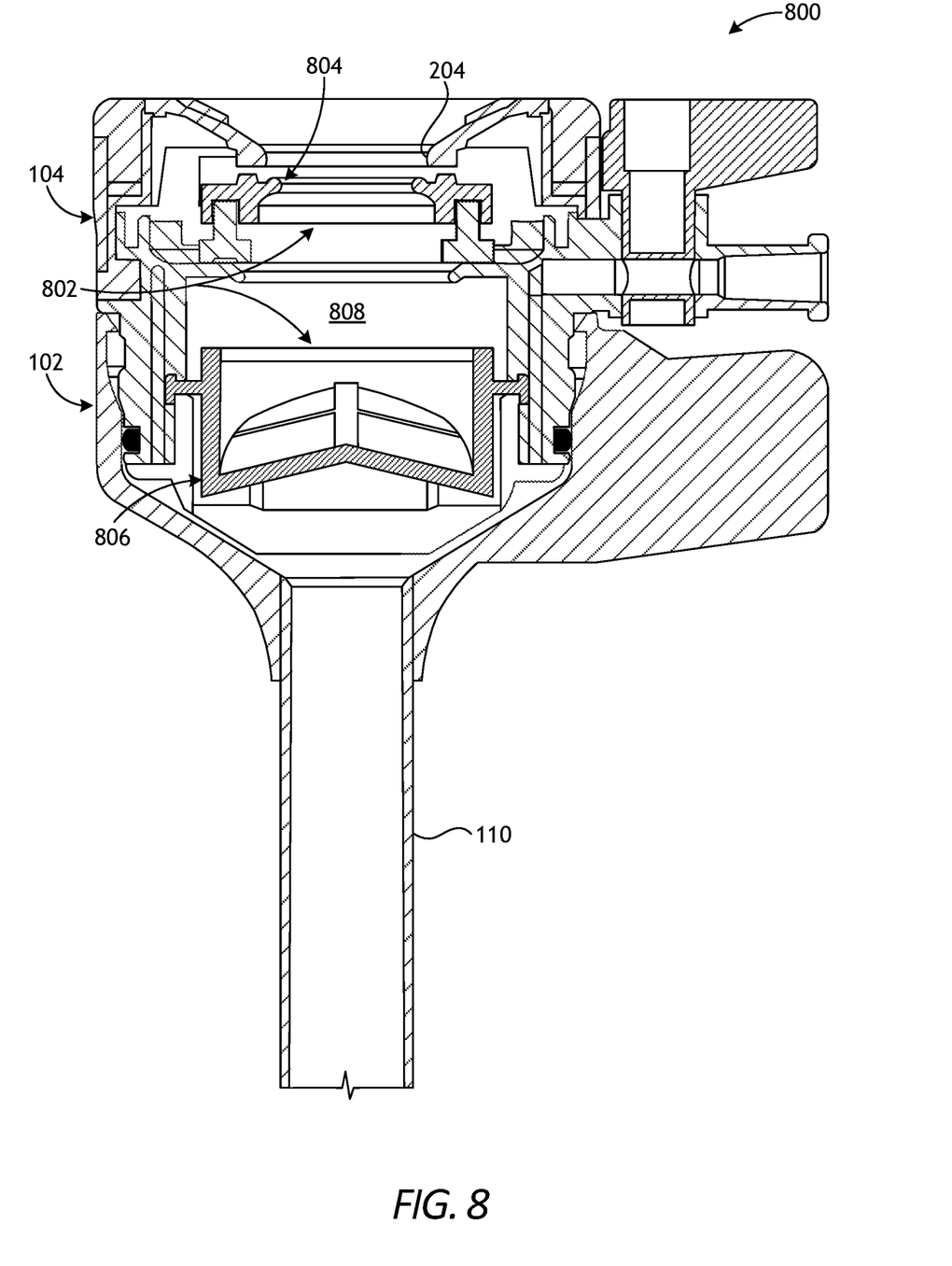
FIG. 8 is an enlarged cross-sectional side view of another example, trocar assembly that may incorporate the principles of the present disclosure.

FIG. 8 is an enlarged cross-sectional side view of another trocar assembly 800 that may incorporate the principles of the present disclosure, according to one or more embodiments. The trocar assembly 800 may be similar in some respects to the trocar assembly 700 of FIG. 7 and therefore may be best understood with reference thereto, where like numerals will represent like components not described again in detail. Similar to the trocar assembly 700 of FIG. 7, the trocar assembly 800 may include the trocar 102 and the seal cartridge 104 at least partially received within the trocar housing 108.

Unlike the trocar assembly 700 of FIG. 7, however, the seal cartridge 104 may include a shaft seal referred to herein as an integral seal system 802 that includes an asymmetric seal 804 axially separated from a duckbill seal 806. The asymmetric and duckbill seals 804, 806 may be similar in structure and function to the asymmetric and duckbill seals 406, 412 of the integral seal system 306 of FIGS. 3, 4A-4B, and 5. The asymmetric and duckbill seals 804, 806 of FIG. 8, however, may comprise independent structures that are axially offset from each other and otherwise arranged at isolated positions within the seal cartridge 104.

The integral seal system 802 is positioned within a central passageway 808 extending axially through the trocar assembly 800. Similar to the central passageway 308 of FIG. 3, the central passageway 808 comprises an elongate pathway that extends axially through the trocar assembly 800 and provides a conduit to guide and introduce surgical tools into an internal body cavity of a patient. In the illustrated embodiment, the central passageway 808 is contiguously defined by the seal cartridge 104 and the trocar 102. Surgical tools may be introduced into the trocar 102 and extended into the cannula 110 by extending through the central orifice 204 and penetrating the integral seal system 802 and, more particularly, successively penetrating the asymmetric and duckbill seals 804, 806. The integral seal system 802 operates similar to the integral seal system 306 of FIGS. 3, 4A-4B, and 5 in that the asymmetric seal 804 may be designed and optimized to complement (offset) the insertion and extraction drag forces generated by the duckbill seal 806. Consequently, the asymmetric seal 804 may be configured to equalize the net drag forces against the surgical tool shaft during insertion and extraction.

Figure 9:
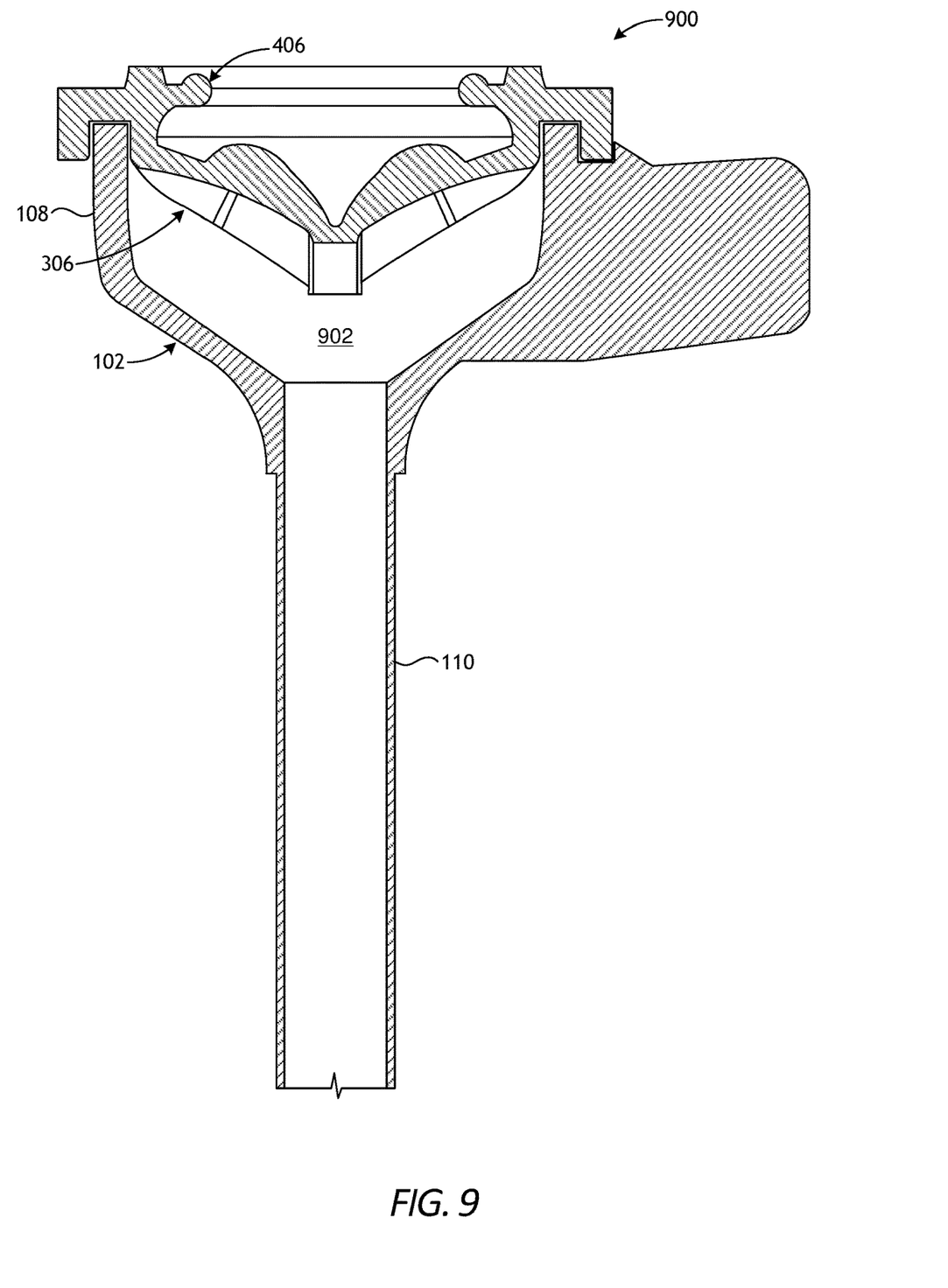
FIG. 9 is an enlarged cross-sectional side view of another example, trocar assembly that may incorporate the principles of the present disclosure.

FIG. 9 is an enlarged cross-sectional side view of another trocar assembly 900 that may incorporate the principles of the present disclosure, according to one or more embodiments. The trocar assembly 900 may be similar in some respects to the trocar assembly 100 of FIGS. 1-3 and therefore may be best understood with reference thereto, where like numerals will represent like components not described again in detail. Similar to the trocar assembly 100 of FIGS. 1-3, the trocar assembly 900 may include the trocar 102. Unlike the trocar assembly 100 of FIGS. 1-3, however, the trocar busing 106 and the seal cartridge 104 are omitted from the trocar assembly 900, and the integral seal system 306 generally described herein may be operatively coupled to the trocar housing 108. In the illustrated embodiment, the integral seal system 306 is mounted at least partially external to the trocar housing 108. In other embodiments, however, it is contemplated herein that the integral seal system 306 may be positioned entirely within the trocar housing 108, such as through a snap fit engagement with the internal walls of the trocar housing 108.

The integral seal system 306 is positioned within a central passageway 902 extending axially through the trocar assembly 900. Similar to the central passageway 308 of FIG. 3, the central passageway 902 comprises an elongate pathway that extends axially through the trocar assembly 900 and provides a conduit to guide and introduce surgical tools into an internal body cavity of a patient. In the illustrated embodiment, the central passageway 902 is contiguously defined by the trocar housing 108 and the cannula 110. Surgical tools may be introduced into the trocar 102 and extended into the cannula 110 by penetrating the integral seal system 306. As generally described above, the asymmetric seal 406 may complement (offset) the insertion and extraction drag forces generated by the duckbill seal 412, which equalizes the net drag forces against the surgical tool shaft during insertion and extraction.

Embodiments disclosed herein include:

A. A trocar assembly that includes a trocar that includes a trocar housing and a cannula that extends distally from the trocar housing, and an integral seal system positioned within a central passageway extending axially through the trocar and engageable against a surgical tool shaft extended therethrough, wherein the integral seal system includes an asymmetric seal and a duckbill seal arranged distal to the asymmetric seal, and wherein the asymmetric seal defines a diaphragm that complements insertion and extraction drag forces generated by the duckbill seal against the surgical tool shaft such that total insertion and extraction drag forces generated by the integral seal system are equalized.

B. A method that includes positioning a trocar assembly adjacent a patient, the trocar assembly including a trocar having a trocar housing and a cannula that extends distally from the trocar housing, and an integral seal system positioned within a central passageway extending axially through the trocar, wherein the integral seal system includes an asymmetric seal with a diaphragm and a duckbill seal arranged distal to the asymmetric seal. The method further includes inserting a surgical tool shaft into the central passageway and thereby penetrating the integral seal system, generating a first insertion drag force as the diaphragm engages the surgical tool shaft, generating a second insertion drag force as the duckbill seal engages the surgical tool shaft, and extracting the surgical tool shaft from the central passageway and thereby generating a first extraction drag force with the diaphragm and a section extraction drag force with the duckbill seal, wherein the first insertion drag force complements the second insertion drag force and the first extraction drag force complements the second extraction drag force such that total insertion and extraction drag forces generated by the integral seal system are equalized.

C. An integral seal system that includes a body that defines a central opening, a duckbill seal extending distally from a bottom of the body and defining one or more parting lines that separate opposing seal flaps, and an asymmetric seal defined by the body and extending radially into the central opening, the asymmetric seal including a diaphragm and an annular flange that extends between the body and the diaphragm, wherein the diaphragm complements insertion and extraction drag forces generated by the duckbill seal against a surgical tool shaft extended therethrough such that total insertion and extraction drag forces generated by the integral seal system are equalized.

Each of embodiments A, B, and C may have one or more of the following additional elements in any combination: Element 1: further comprising a seal cartridge releasably coupled to the trocar, and a trocar bushing releasably coupled to the seal cartridge and including a reducer shaft extendable through the seal cartridge and into the cannula, wherein the central passageway is defined by the trocar bushing. Element 2: wherein the integral seal system is arranged at a proximal end of the reducer shaft. Element 3: further comprising a seal cartridge releasably coupled to the trocar, wherein the central passageway is contiguously defined by the seal cartridge and the trocar, and wherein the diaphragm complements insertion and extraction drag forces generated by the duckbill seal and an additional seal arranged within the seal cartridge such that the total insertion and extraction drag forces generated by the integral seal system and the additional seal are equalized. Element 4: further comprising a seal cartridge releasably coupled to the trocar, wherein the central passageway is contiguously defined by the seal cartridge and the trocar, and wherein the asymmetric seal and the duckbill seal comprise independent structures axially offset from each other within the central passageway. Element 5: wherein the integral seal system is mounted to the trocar housing. Element 6: wherein the integral seal system comprises a body that defines a central opening and the asymmetric seal is defined by the body and extends radially into the central opening, and wherein the duckbill seal extends distally from a bottom of the body. Element 7: wherein an annular flange extends between the body and the diaphragm. Element 8: wherein the asymmetric seal generates larger drag forces during tool insertion and smaller drag forces during tool extraction, and wherein the duckbill seal generates smaller drag forces during tool insertion and larger drag forces during tool extraction. Element 9: wherein the diaphragm exhibits a cross-sectional shape selected from the group consisting of bulbous, spherical, polygonal, pyramidal, conical, frustoconical, ovoid, and any combination or plurality thereof. Element 10: wherein the diaphragm protrudes proximally relative to the duckbill seal.

Element 11: wherein the trocar assembly further includes a seal cartridge releasably coupled to the trocar, and a trocar bushing releasably coupled to the seal cartridge and including a reducer shaft extendable through the seal cartridge and into the cannula, and wherein the central passageway is defined by the trocar bushing. Element 12: wherein the trocar assembly further includes a seal cartridge releasably coupled to the trocar, and wherein the central passageway is contiguously defined by the seal cartridge and the trocar, the method further comprising generating a third insertion drag force as an additional seal arranged within the seal cartridge engages the surgical tool shaft, generating a third extraction drag force with the additional seal as the surgical tool is extracted, and complementing the second and third insertion drag forces with the first insertion drag force, and complementing the second and third extraction drag forces with the first extraction drag force such that the total insertion and extraction drag forces generated by the integral seal system and the additional seal are equalized. Element 13: wherein the trocar assembly further includes a seal cartridge releasably coupled to the trocar and the central passageway is contiguously defined by the seal cartridge and the trocar, and wherein the asymmetric seal and the duckbill seal comprise independent structures axially offset from each other within the central passageway. Element 14: wherein the integral seal system is mounted to the trocar housing.

Element 15: wherein the asymmetric seal is engageable with the surgical tool shaft and generates larger drag forces during tool insertion and smaller drag forces during tool extraction, and wherein the duckbill seal generates smaller drag forces during tool insertion and larger drag forces during tool extraction. Element 16: wherein the diaphragm exhibits a cross-sectional shape selected from the group consisting of bulbous, spherical, polygonal, pyramidal, conical, frustoconical, ovoid, and any combination or plurality thereof. Element 17: wherein the body is made from an elastic or pliable material selected from the group consisting of rubber, silicone, ethylene vinyl acetate, nylon, vinyl, spandex, polyurethane, polyethylene, polypropylene, polyisoprene, and any combination thereof.

By way of non-limiting example, exemplary combinations applicable to A, B, and C include: Element 1 with Element 2; and Element 6 with Element 7.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An integral seal system, comprising:
   a body that defines a central opening and comprises a proximal end and a distal end;
   an asymmetric seal extending into the central opening, the asymmetric seal including a diaphragm and an annular flange that extends between the proximal end of the body and the diaphragm, wherein the diaphragm has a cross-sectional thickness larger than a cross-sectional thickness of the annular flange; and
   a duckbill seal extending distally from the distal end of the body and defining one or more parting lines that separate opposing seal flaps,
   wherein the diaphragm complements insertion and extraction drag forces generated by the duckbill seal against a surgical tool shaft extended therethrough such that total insertion and extraction drag forces generated by the integral seal system are equalized,
   wherein, when in a relaxed state, the diaphragm projects from the annular flange in a proximal direction, towards the proximal end and away from the duckbill seal, and
   wherein the asymmetric seal and the duckbill seal are formed together as a single structure.

2. The integral seal system of claim 1, wherein the asymmetric seal is engageable with the surgical tool shaft and generates larger drag forces during tool insertion and smaller drag forces during tool extraction, and wherein the duckbill seal generates smaller drag forces during tool insertion and larger drag forces during tool extraction.

3. The integral seal system of claim 1, wherein the diaphragm exhibits a cross-sectional shape selected from the group consisting of bulbous, spherical, polygonal, pyramidal, conical, frustoconical, ovoid, and any combination or plurality thereof.

4. The integral seal system of claim 1, wherein the body is made from an elastic or pliable material selected from the group consisting of rubber, silicone, ethylene vinyl acetate, nylon, vinyl, spandex, polyurethane, polyethylene, polypropylene, polyisoprene, and any combination thereof.

5. The integral seal system of claim 1, wherein the asymmetric seal is defined by the body.

6. The integral seal system of claim 1, wherein the diaphragm exhibits a bulbous cross-section.

7. The integral seal system of claim 1, wherein a diameter of the diaphragm is greater than a thickness of the annular flange.

8. The integral seal system of claim 1, wherein the diaphragm exhibits a bulbous cross-section, and wherein a diameter of the bulbous cross-section is greater than a thickness of the annular flange.

9. An integral seal system, comprising:
a body that defines a central opening;
an asymmetric seal extending into the central opening and including a diaphragm and an annular flange that extends between the body and the diaphragm, wherein the diaphragm has a cross-sectional thickness larger than a cross-sectional thickness of the annular flange; and
a duckbill seal axially spaced and separated from the asymmetric seal and defining one or more parting lines that separate opposing seal flaps,
wherein the diaphragm complements insertion and extraction drag forces generated by the duckbill seal against a surgical tool shaft extended therethrough such that total insertion and extraction drag forces generated by the integral seal system are equalized,
wherein, when in a relaxed state, the diaphragm projects from the annular flange in a proximal direction away from the duckbill seal, and
wherein the asymmetric seal and the duckbill seal are formed together as a single structure.

10. The integral seal system of claim 9, wherein the diaphragm protrudes proximally relative to the annular flange.

11. The integral seal system of claim 9, wherein the asymmetric seal is engageable with the surgical tool shaft and generates larger drag forces during tool insertion and smaller drag forces during tool extraction, and wherein the duckbill seal generates smaller drag forces during tool insertion and larger drag forces during tool extraction.

12. The integral seal system of claim 9, wherein the diaphragm exhibits a cross-sectional shape selected from the group consisting of bulbous, spherical, polygonal, pyramidal, conical, frustoconical, ovoid, and any combination or plurality thereof.

13. The integral seal system of claim 9, wherein the body is made from an elastic or pliable material selected from the group consisting of rubber, silicone, ethylene vinyl acetate, nylon, vinyl, spandex, polyurethane, polyethylene, polypropylene, polyisoprene, and any combination thereof.

14. The integral seal system of claim 9, wherein the asymmetric seal is defined by the body.

15. A method, comprising:
penetrating an integral seal system with a surgical tool shaft, the integral seal system including:
a body that defines a central opening;
an asymmetric seal extending into the central opening and including a diaphragm and an annular flange that extends between the body and the diaphragm, wherein the diaphragm has a cross-sectional thickness larger than a cross-sectional thickness of the annular flange; and
a duckbill seal axially spaced from the asymmetric seal and defining one or more parting lines that separate opposing seal flaps, wherein, when in a relaxed state, the diaphragm projects from the annular flange in a proximal direction away from the duckbill seal, and wherein the asymmetric seal and the duckbill seal are formed together as a single structure;
generating a first insertion drag force as the diaphragm engages the surgical tool shaft;
generating a second insertion drag force as the duckbill seal engages the surgical tool shaft; and
extracting the surgical tool shaft from the central passageway and thereby generating a first extraction drag force with the diaphragm and a section extraction drag force with the duckbill seal,
wherein the first insertion drag force complements the second insertion drag force and the first extraction drag force complements the second extraction drag force such that total insertion and extraction drag forces generated by the integral seal system are equalized.

16. The method of claim 15, further comprising:
generating a first drag force with the asymmetric seal during tool insertion; and
generating a second drag force with the asymmetric seal during tool extraction, wherein the first drag force is greater than the second drag force.

17. The method of claim 15, wherein the duckbill seal extends distally from a bottom of the body.

18. The method of claim 15, wherein the duckbill seal is axially separated from the asymmetric seal.

19. The method of claim 15, wherein the diaphragm protrudes proximally relative to the annular flange.

* * * * *